United States Patent [19]

Schwartz et al.

[11] Patent Number: 5,204,249
[45] Date of Patent: Apr. 20, 1993

[54] PROCESS FOR THE PREPARATION OF CAREBASTINE AND SIMILAR MATERIALS

[75] Inventors: Harry Schwartz, Hofheim-Diedenbergen; Henning Böttcher, Darmstadt, both of Fed. Rep. of Germany

[73] Assignee: Merck Patent Gesellschaft Mit Beschrankter Haftung, Fed. Rep. of Germany

[21] Appl. No.: 783,024

[22] Filed: Oct. 25, 1991

[30] Foreign Application Priority Data

Oct. 27, 1990 [DE]  Fed. Rep. of Germany ....... 4034218

[51] Int. Cl.⁵ .................... C12P 17/12; C12N 1/14; C07D 211/46
[52] U.S. Cl. .................................. 435/122; 435/911
[58] Field of Search ............................ 435/122, 911

[56] References Cited

U.S. PATENT DOCUMENTS

| | | | |
|---|---|---|---|
| 3,822,188 | 7/1974 | Fager et al. | 435/911 |
| 4,064,009 | 12/1977 | Fukuda et al. | 435/125 |
| 4,153,509 | 5/1979 | Schwartz | 435/129 |
| 4,996,149 | 2/1991 | Jarreau et al. | 435/119 |

FOREIGN PATENT DOCUMENTS 134124  3/1985  European Pat. Off. .

OTHER PUBLICATIONS

ATCC "Catalogue of Fungi/Yeasts" 17th Ed. 1987 pp. 126–127.

*Primary Examiner*—Herbert J. Lilling
*Attorney, Agent, or Firm*—Millen, White, Zelano & Branigan

[57] ABSTRACT

The invention relates to a novel process for the preparation of carebastine and similar materials from ebastine or terfenadine by oxidization using microorganisms. Carebastine and similar materials are used for the treatment of allergic disorders and as antihistamines.

4 Claims, No Drawings

PROCESS FOR THE PREPARATION OF CAREBASTINE AND SIMILAR MATERIALS

The invention relates to a novel process for the preparation of carebastine and similar materials characterized in that ebastine or corresponding starting materials are oxidized with a microorganism.

The chemical preparation of carebastine (p-[4-[4-(diphenylmethoxy)piperidino]butyryl]-2-methylhydratropic acid) is disclosed in EP 134 124 but in this method an ester derivative is hydrolyzed.

SUMMARY OF THE INVENTION

This invention provides an improved process for the preparation of carebastine and similar materials, which have pharmaceutical value.

It has been found that ebastine and other related materials are, surprisingly, oxidized by microorganisms selectively to carebastine and other corresponding products. This novel process has the advantage by comparison with the known process that it provides direct straightforward access to carebastine and other materials avoiding multistage chemical syntheses with far lower selectivity. In addition, the novel method can easily be transferred to industrial scale and therefore has the advantage by comparison with the conventional process that, e.g., carebastine can be obtained therewith for the first time in relatively large amounts.

The process is also suitable for the oxidation of similar compounds, especially for the oxidation of terfenadine. The process is conducted analogously as the process for preparing carebastine. The oxidation of terfenadine yields a carboxylic acid derivative, α-[4-(2-carboxy-propyl-2)-phenyl]-4-(hydroxy-diphenyl-methyl)-1-piperidino-butanol.

Compounds similar to ebastine or terfenadine for oxidation in accordance with this invention include compounds of the type $R-C(CH_3)_3$, wherein R is:

The activity of ebastine and terfenadine and the products of the reaction of this invention, e.g., as antihistamines, are discussed in "Drugs of the Future", Vol. 15, No. 7, pp. 674-679 (1990); Woodward, J.K., Munro, N.L., "Terfenadine, the first non-sedating antihistamine", Arzneim-Forsch/Drug Research 1982, 32:1154-6; Roberts, D.J., Spickett, R.G.W., Moragues, J., Celdran, "Ebastine, a new non-sedative antihistamine". Xth Int. Cong. Pharmacol. (Aug. 23-28, Sydney) 1987, Abst P1006, Garticz, D.A., Hook, R.H., Walker, B.J., Okerholm, R.A. "Pharmacokinetics and biotransformation studies of terfenadine in man". Arzneim-Forsch/Drug Res 1982, 32:1185-90; Torrent, J., Barbanoj, M.J., Izquierdo, I., Sequra, J., Jane, F. "Ebastine pharmacokinetics and antihistamine effect in man." XIII Int. Cong. Allergol. Clin. Immunol. (Oct. 16-20, Montreaux).

The corresponding carboxylic acid derivatives prepared by the process of this invention as applied to the foregoing substituted analogs also have antihistaminic activity analogous to that described in these references.

Carebastine and the similar materials produced by this invention can thus be used as active substances in pharmaceuticals in human and veterinary medicine, especially as antiallergics, antihistamines, and for the treatment of cardiovascular disorders.

The invention furthermore relates to the use of microorganisms, preferably of filamentous fungi, preferably of the genus Cunninghamella, especially of the species *Cunninghamella elegans*, but also *Cunninghamella blakesleeana*, , for the chemoselective oxidation of ebastine or terfenadine or the related materials discussed herein.

In detail, ebastine or terfenadine or other material are expediently added directly or in solution, preferably in dimethylformamide (DMF), but also in dimethyl sulfoxide (DMSO), dimethylacetamide (DMA), dimethoxyethane (DME), tetrahydrofuran (THF) and dibutyl-, diisopropyl-, diethylformamide, 1-methyl-, 1-ethyl-,

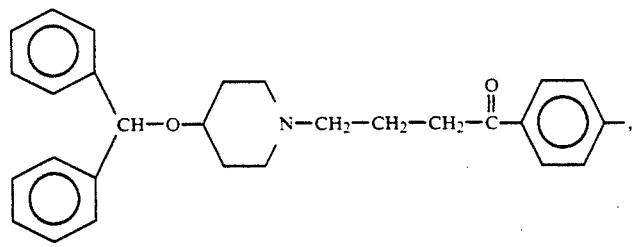

or

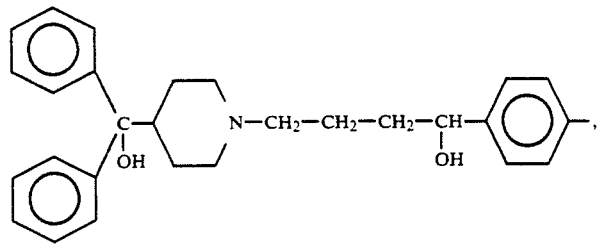

the corresponding structural portions of ebastine and terfenadine, respectively, but wherein any or all of the phenyl groups and/or piperidinyl group is/are substituted by alkyl, alkoxy or halo (F. Cl, Br, I), wherein the alkyl portion has 1-6 carbon atoms.

1-cyclohexylpyrrolidone, 4-formyl-morpholine, 1-formylpiperidine, 1-formylpyrrolidine, tetramethyl-tetraethyl-, tetrabutylurea, tripiperidino-, tripyrrolidinophosphine oxide, sulfolane or N-methyl-caprolactam or mixtures of the said solvents, at a pH between 3 and 9, but especially in the neutral range, to a culture solution of the microorganisms, which is prepared by processes known per se, and incubated at a temperature between about 10° and 60° C., preferably 25°-35° C., for 2-200 hours, preferably 1 week. Conventional procedures disclosed in Crueger, W. and A. Crueger, *Biotechnology: A Textbook of Industrial Microbiology* (1984); Demain, A.L. and N. A. Solomon, *Manual of Industrial Microbiology and Biotechnology* (1986) are applicable to preparing the cultures and carrying out the oxidation. Specifically, the microorganism cultures can be prepared as follows:

The microorganisms are propagated in a neutral culture medium consisting of peptone (soya-meal), yeast-extract, NaCl, $K_2HPO_4$ and glucose over a period of 24 hours at temperatures between 20° and 40° C.

The microorganisms *Cunninghamella blakesleeana* (DSM 1906) and *Cunninghamella elegans* (DSM 1908) used in the present invention are freely available from Deutsche Samnlung von Mikroorganismen und Zell-kulturen GmbH (DSM) German Collection of Microorganisms and Cell Cultures), Mascherder Weg IB, D-3300 Braunschweig, Germany.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application Federal Republic of Germany P 40 34 218.2, filed Oct. 27, 1990, are hereby incorporated by reference.

EXAMPLES

Example 1

0.05 1 of culture solution (pH 7.0) is inoculated with *Cunninghamella elegans* (DSM 1908). After culturing at 28° C. for three days, 50 mg of ebastine dissolved in 0.5 ml of DMF are added. After further incubation at 28° C. for 5 days, the resulting suspension is acidified with HCl and extracted with dichloromethane. The organic phase is dried over sodium sulfate and then the solvent is removed. The carebastine obtained as residue is purified by preparative TLC or column chromatography (dichloromethane/methanol 10:1; silica gel); melting point 93°-95° C.

Example 2

*Cunninghamella blakesleeana* (ATCC 8688a) is cultivated in 1 of culture solution at a pH of 7. 0.5 g of ebastine dissolved in 5 ml of DMF is added to the culture. The incubation is carried out at 30° C. for 1 week. Working up in analogy to Example 1 yields carebastine; melting point 93°-95° C.

Example 3

0.2 g of ebastine dissolved in 2 ml of DMSO is added to 1 of culture solution of *Cunninghamella elegans* (DSM 1908) at pH 6. After incubation at 30° C. for 4 days, working up is carried out in analogy to Example 1, and carebastine is obtained; melting point 93°-95° C.

Example 4

The experiment is carried out in analogy to Example 1 in a 100 1 reactor by adding 5 g of ebastine dissolved in 50 ml of DMF to 100 1 of culture solution of *Cunninghamella elegans* (DSM 1908). working up in analogy to Example 1 yields carebastine; melting point 93°-95° C.

Example 5

*Cunninghamella blakesleeana* (ATCC 8688a) is cultivated in 1 of culture solution for 3 days. The cells are thoroughly washed and separated from the nutrient medium, washed and separated from the nutrient medium, washed twice in phosphate buffer (0.1 M; pH 7.2) and resuspended in the same buffer. 0.1% ebastine is added to the cell suspension. After incubation at 28° C. for 7 days, working up is carried out in analogy to Example 1. Carebastine is obtained; melting point 93°-95° C.

Example 6

*Cunninghamella elegans* (DSM 1908) is employed in place of *Cunninghamella elegans* (ATCC 8688a) in analogy to Example 5. Culturing, incubating and working up in accordance with Example 5 yields carebastine; melting point 93°-95° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of carebastine and similar materials comprising microbiologically oxidizing compounds of formula I:

wherein

R =

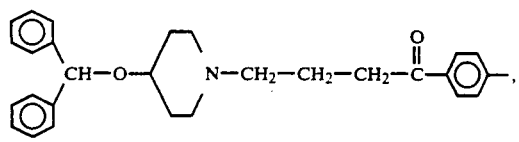

or

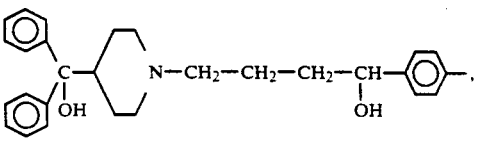

wherein any or all of the phenyl groups and/or piperidinyl groups is/are substituted by alkyl, alkoxy or halo and wherein alkyl portion has 1-6 carbon atoms; with a

*Cunninghamella blakesleeana* or *Cunninghamella elegans* and recovering the oxidized product.

2. A process of claim 1, comprising incubating the *Cunninghamella blakesleeana* or *Cunninghamella elegans* at 10°–60° C. for 2–200 hours.

3. A process of claim 1, wherein the product is carebastine.

4. A process of claim 1, wherein the product is α-[4-2-carboxy-propyl-2-)-phenyl)-4-(hydroxy-diphenyl-methyl) -1-piperidino butanol.

* * * * *